(12) United States Patent
Ueno et al.

(10) Patent No.: US 6,403,827 B1
(45) Date of Patent: Jun. 11, 2002

(54) CRYSTAL OF 2-HYDROXYNAPHTHALENE-3-CARBOXYLIC ACID AND PROCESS FOR THE PREPARATION THEREOF

(75) Inventors: Ryuzo Ueno, Nishinomiya; Masaya Kitayama, Takarazuka; Nobutaka Izumichi, Ashiya; Hiroyuki Kato, Kawanishi, all of (JP)

(73) Assignee: Kabushiki Kaisha Ueno Seiyaku Oyo K., Osaka (JP)

( * ) Notice: Subject to any disclaimer, the term of this patent is extended or adjusted under 35 U.S.C. 154(b) by 0 days.

(21) Appl. No.: 09/720,994
(22) PCT Filed: May 1, 2000
(86) PCT No.: PCT/JP00/02862
§ 371 (c)(1),
(2), (4) Date: Jan. 3, 2001
(87) PCT Pub. No.: WO00/68177
PCT Pub. Date: Nov. 16, 2000

(30) Foreign Application Priority Data

May 7, 1999 (JP) .......................................... 11-127158

(51) Int. Cl.$^7$ ................................................ C07C 63/34
(52) U.S. Cl. ........................................ 562/467; 560/56
(58) Field of Search ......................................... 562/467

(56) References Cited

FOREIGN PATENT DOCUMENTS

| | | | |
|---|---|---|---|
| GB | 2008090 | * | 5/1979 |
| JP | 55-35042 | | 3/1980 |

* cited by examiner

Primary Examiner—Paul J. Killos
(74) Attorney, Agent, or Firm—Sughrue Mion, PLLC

(57) ABSTRACT

The present invention provides crystalline 2-hydroxynaphthalene-3-carboxylic acid (BON) characterized in that the average particle size is equal to or more than 157 μm and the proportion of the particles of which particle size is less than 74 μm is equal to or less than 14%. The crystalline composition of the present invention can be prepared by a process comprising the step of recrystallizing BON, especially at a high temperature, or by carrying out the acid precipitation step in the method for preparing BON at a high temperature.

7 Claims, No Drawings

CRYSTAL OF 2-HYDROXYNAPHTHALENE-3-CARBOXYLIC ACID AND PROCESS FOR THE PREPARATION THEREOF

TECHNICAL FIELD

The present invention provides a crystalline 2-hydroxynaphthalene-3-carboxylic acid having significantly suppressed dusting tendency, and a process for preparing the same.

BACKGROUND ART 2-hydroxynaphthalene-3-carboxylic acid is important as an intermediate for pigments or dyes. Generally, it is prepared by reacting β-naphthol with sodium hydride to give sodium β-naphtholate, reacting the resulting compound with carbon dioxide under pressure to give sodium 2-hydroxynaphthalene-3-carboxylate and then, isolating the desired compound by means of acid precipitation i.e. by adding a mineral acid to the salt.

For a long time, the Kolbe-Schmitt reaction, a solid-gas phase reaction, had been employed for the reaction between sodium β-naphtholate and carbon dioxide. Said reaction, however, had some problems, such as more than 50 hours of long reaction time was required, high amount of β-naphthol was wasted because of thermal heterogeneity at the high reaction temperature, controlling the reaction was difficult due to the phase conversion and a stable yield was hardly obtained. In order to solve those problems, a number of methods including a method using reaction media had been proposed.

One of the present inventors had invented a process comprising the step of reacting a liquid mixture consisting of light oil or kerosene, sodium β-naphtholate and β-naphthol, with carbon dioxide (Japanese Patent Publication (KOKOKU) No. 53296/1981) and said process has been industrially used at present. This process can be carried out successively and can provide 2-hydroxynaphthalene-3-carboxylic acid with very low amount of impurities and with highly stable quality. According to said method, 2-hydroxynaphthalene-3-carboxylic acid with high quality, such as those having 220–221° C. of melting point and 99.5% of purity and containing only 0.03% of sodium β-naphtholate, can be obtained. In the process, 2-hydroxynaphthol-3-carboxylic acid is isolated from the mother liquid by means of acid precipitation, filtration, centrifugation and the like, washed with water, dried and then, is used as an intermediate for pigments or dyes.

Crystalline composition of 2-hydroxynaphthalene-3-carboxylic acid usually comprises very fine particles and, therefore, is highly dusty. In addition to the dusting tendency, due to the severe mucosal irritativeness of 2-hydroxynaphthalene-3-carboxylic acid, handling of the compound is highly obstructed. For example, when 2-hydroxynaphthalene-3-carboxylic acid is added into a reaction tank as an intermediate for a pigment or dye, fine particles of 2-hydroxynaphthalene-3-carboxylic acid fly in the air as powdery dust. The fine particles of 2-hydroxynaphthalene-3-carboxylic acid flown in the air are hardly precipitated, disperse widely, pollute the environment, and stimulate the skin and mucosa of the operators to make them uncomfortable. In order to diminish the problems concerning workability and safety in the feeding step, operators wear dust-proof glasses and masks and the reactor is mounted a vacuum at a position other than the supply port to deaerate the fine particles and a filter to trap the same. However, they are not enough.

The reason why 2-hydroxynaphthalene-3-carboxylic acid dusts significantly is believed that said compound consists of very fine crystalline particles, and that said compound is hardly dissolved in water and, therefore, hardly uptakes moisture; and therefore, each crystalline particles do not agglomerate or bind together through the free water. As a consequence, the fine crystalline particles move individually upon an external impact. In order to suppress the dusting tendency of the material having the above-described characteristics, Japanese patent Application Laid Open No. 196841/1983 discloses a method for granulating 2-hydroxynaphthalene-3-carboxylic acid particles. Although thus obtained granulated 2-hydroxynaphthalene-3-carboxylic acid particles exhibited suppressed dusting tendency, said process is highly complicated, that is, comprises the steps of adding a determined amount of water to 2-hydroxynaphthalene-3-carboxylic acid and controlling the water content of acid precipitated 2-hydroxynaphthalene-3-carboxylic acid by centrifugation and therefore was not suitable for mass production.

Further, Japanese Patent Application Laid Open NO. 212533/1986 discloses a process for preparing granule comprising the step of granulating 2-hydroxynaphthalene-3-carboxylic acid together with an aqueous mixture containing a hydrophilic organic solvent having lower boiling point such as a lower alcohol. In this process, the step to add the organic solvent is required and therefore, the whole process becomes longer.

Accordingly, the object of the present invention is to solve the above-mentioned problems and to provide crystalline 2-hydroxynaphthalene-3-carboxylic acid with well-suppressed dusting tendency.

DISCLOSURE OF INVENTION

The present invention provides a crystalline composition of 2-hydroxynaphthalene-3-carboxylic acid with a extremely suppressed dusting tendency, having an average particle size of equal to or more than 175 $\mu$m and the proportion of the particles of which particle size are equal to or less than 74 $\mu$m is equal to or less than 14%.

In the present specification and claims, each "%" represents weight % except for indicated particularly.

In the present specification and claims, the average particle size means the value determined as below:

The sample material is weighted and then is sequentially screened with sieves having aperture of 710 $\mu$m, 297 $\mu$m, 170 $\mu$m, 106 $\mu$m, 74 $\mu$m and 45 $\mu$m in this order. The residue on the respective sieves and the amount of passed the 45 $\mu$m sieve were weighed. The average particle size is calculated as follows:

average particle size ($\mu$m)=(710×residue on the 710 $\mu$m sieve (wt %)/100)+(297×residue on the 297 $\mu$m sieve (wt %)/100)+(170×residue on the 170 $\mu$m sieve (wt %)/100)+ (106×residue on the 106 $\mu$m sieve (wt %)/100)+

(74×residue on the 74 $\mu$m sieve (wt %)/100)+(45×residue on the 45 $\mu$m sieve (wt %)/100)+(25×passed the 45 $\mu$m sieve (wt %)/100).

The crystalline particles of 2-hydoroxynaphthalene-3-carboxylic acid having the characteristics recited in the present invention are more than 2–4.5 times as large as the conventional crystalline 2-hydoroxynaphthalene-3-carboxylic acid particles. The crystalline composition of the present invention exhibits significantly suppressed dusting tendency, and therefore, is easy for handling with significantly reduced risk to environment and human beings. Further, said crystalline particles of the present invention can easily be pulverized into fine particles and exhibit the dissolution rate comparative to the conventional small size (50–90 μm) crystalline particles. That is, the crystalline composition of the present invention may preferably be used as intermediate of pigments or dyes.

The large-size crystalline 2-hydroxynaphthalene-3-carboxylic acid of the present invention preferably possesses chromaticity of, 38–69 of lightness and 4.6–18.0 of whiteness.

"Chromaticity" used herein means a property of a color stimulus determined by chromaticity coordinates or by combination of dominant wavelength or complementary wavelength and purity (JIS Z 8120).

"Lightness" means an attribute of a color in respect of relative contrast of the surface of an object, which is classified on the basis of white surface that is illuminated by same condition (JIS Z 8105). In the present specification and claims, "lightness" represents L value of the "Lab" color representation system, which is well known in the art. The Lab values are calculated by the following formula from tristimulus values (X, Y, Z) measured according to JIS Z 8722:

$$L=10(Y)^{1/2}$$

$$a=17.5(1.02X-Y)/(Y)^{1/2}$$

$$b=7.0(Y-0.847Z)/(Y)^{1/2}$$

"Whiteness" is a number of one-dimensional value representing the degree of white of the surface of an object (JIS Z 8105). In the present specification and claims, "whiteness" represents the value calculated from the above described tristimulus values by the following formula:

$$\text{Whiteness}=Z/1.1823.$$

The crystalline 2-hydroxynaphthalene-3-carboxylic acid of the present invention can be prepared by recrystallizing 2-hydroxynaphthalene-3-carboxylic acid at high temperature. The starting material of crystalline 2-hydroxynaphthalene-3-carboxylic acid may be prepared by any of conventional processes. For example, said starting material may be prepared by acid precipitating at 80–100° C. 2-hydroxynaphthalene-3-carboxylic acid alkaline metal salt which is obtained by the Kolbe-Schmitt method described in Japanese Patent Publication (KOKOKU) No. 53296/1981.

The high temperature recrystallizing step may preferably be carried out immediately after acid precipitation of 2-hydroxynaphthalene-3-carboxylic acid. The aqueous 2-hydroxynaphthalene-3-carboxylic acid solution obtained by the acid precipitating step may be added with water, a water-soluble solvent or a water insoluble solvent, stirred and heated to a temperature higher than 100° C. under pressure. The temperature and pressure may be kept for 5 to 30 minutes and then, the mixture may be cooled to 50–90° C. After that, the solvent may be removed by centrifugation and the precipitate may be washed with water and dried to provide the desired crystalline composition.

Water, a water-soluble solvent or a water-insoluble solvent may be added to the solution independently or in combination. Examples of water-soluble solvent include methanol, ethanol, 1-propanol and isopropylalcohol. Examples of water-insoluble solvent include acetophenone, cyclohexane and ethylhexylalcohol. When the recrystallization process is carried out by adding a solvent to the aqueous solution of 2-hydroxynaphthalene-3-carboxylic acid or sodium salt thereof, said solution may contain 7–20%, preferably 8–16%, more preferably 9–13% of said acid or salt. The amount of the solvent to be added may be 2–50%, preferably, 4–40%, and more preferably 10–30% of the total amount of the aqueous solution.

The high temperature recrystallizing step may be carried out at a temperature higher than 100° C., preferably 120–180° C., more preferably 120–160° C. and at a pressure of 0.1–20 kg/cm$^2$(G), preferably 0.2–14 kg/cm$^2$(G), more preferably 0.5–8 kg/cm$^2$(G).

Thereafter, in the cooling step, the temperature may be declined at the rate of 4° C./min–0.1° C./min., preferably 2° C./min.–0.2° C./min.

In another embodiment, the crystalline 2-hydroxynaphthalene-3-carboxylic acid of the present invention may be prepared by operating the acid precipitation process at a temperature higher than 120° C. in the process for preparing 2-hydrocynaphthalene-carboxylic acid comprising the step of acid precipitating an alkaline metal salt of 2-hydroxynaphthalene-3-carboxylic acid. This embodiment can be practiced based on the conventional step by only raising the temperature of the acid precipitation step. Therefore, the conventional system can be easily adopted to practice the embodiment.

According to the conventional Kolbe-Schmitt method, the solution before being subjected to the acid precipitating step generally contains 7–20% of the alkaline metal salt of 2-hydroxynaphthalene-3-carboxylic acid. In this embodiment, the aqueous solution of 2-hydroxynaphthalene-3-carboxylic acid alkaline metal salt containing said amount of the salt may be stirred and heated to a temperature higher than 120° C. under pressure, and then the pH of the solution may be adjusted to 1–4 with sulfuric acid. After the pH is adjusted, the mixture may be cooled to 50–90° C., the solvent may be removed by centrifugation, and the residue may be washed with water and dried to provide the desired crystalline composition.

In this embodiment, the acid precipitating step may be carried out at a temperature higher than 120° C., preferably, 120–180° C., more preferably, 120–160° C. When the temperature is lower than 120° C., the particle size of the obtained crystalline 2-hydroxynaohthalene-3-carboxylic acid will be reduced and therefore, the effect to suppress dusting cannot be achieved. On the other hand, when the temperature of the acid precipitating step is higher than 180° C., 2-hydroxynaphthalene-3-carboxylic acid may be decomposed and the yield may be declined.

The pressure during the acid precipitating step may be 0.1–10 kg/cm$^2$(G), preferably, 0.2–5 kg/cm$^2$(G), more preferably, 0.5–3 kg/cm$^2$(G). The cooling step may be carried out as the same manner as in the above-described high temperature recrystallization embodiment.

In order to obtain the large size crystalline 2-hydroxynaphthalene-3-carboxylic acid of the present invention, acids used in the acid precipitating step are not limited, but preferably are mineral acids or sulfuric acid. Examples of mineral acids include binary acids (hydro acids) such as hydrochloric acid and hydrofluoric acid and oxo acids such as nitric acid, phosphoric acid and perchloric acid. The pH of the acid precipitating step may preferably be adjusted between 1 and 4.

In a further embodiment, the crystalline 2-hydroxynaphthalene-3-carboxylic acid of the present invention may be prepared by recrystallizing crystalline 2-hydroxynaphthalene-3-carboxylic acid obtained by means of the conventional acid precipitation process. This recrystallization may be carried out at an ambient or high pressure, and water, water-soluble solvent or water insoluble solvent may be used as above independently or in combination. Especially, a mixed solvent of water and methanol is preferable.

Generally, crystalline 2-hydroxynaphthalene-3-carboxylic acid may be prepared by means of acid precipitation of crude 2-hydroxynaphthalene-3-carboxylic acid, which may be obtained by a conventional method such as the Kolbe-Schmitt method described in Japanese Patent Publication No. 53296/1980. The crude 2-hydroxynaphthalene-3-carboxylic acid used herein is generally comprises more than 80 wt % of 2-hydroxynaphthalene-3-carboxylic acid, and impurities such as 2-hydroxynaphthalene-6-carboxylic acid, 2-hydroxynaphthalene-3,6-dicarboxylic acid and unreacted β-naphthol. In order to use as an intermediate for pigments or dyes, 2-hydroxynaphthalene-3-carboxylic acid is preferably purified to 98 wt % or higher purity.

The average particle size of the crystalline 2-hydroxynaphthalene-3-carboxylic acid of the present invention is equal to or higher than 157 μm, and is preferably 167–367 μm. When the average particle size is less than 157 μm, the effect to suppress dusting cannot be achieved. The crystalline composition may contain particles of which particle sizes are equal to or less than 74 μm up to 14%, preferably, up to 6% of the total amount of the composition. When the proportion of the particles of which particle sizes are equal to or less than 74 μm is more than 14%, the crystalline composition becomes to exhibit high dusting tendency due to those small size particles.

Further, the proportion of most high frequent particle size of the crystalline composition of the present invention may preferably be between 170–297 μm. The proportion of the particles of which particle sizes are higher than 297 μm may be 14–89%, preferably 28–80%.

Examples of the present invention will be illustrated below.

EXAMPLE 1

To a 1 L autoclave, 800 g of aqueous solution containing 100 g of sodium 2-hydroxynaphthalene-3-carboxylate prepared by means of the Kolbe-Schmitt method was fed and heated to 160° C. An aqueous sulfuric acid solution (72%) was added dropwise to the solution over 50 minutes to adjust the pH of the mixture to 3.5. Then, the mixture was cooled to 80° C. at the rate of 0.4° C./min. At the same temperature, the mixture was filtrated to give 80.6 g of crystalline 2-hydroxynaphthalene-3-carboxylic acid.

EXAMPLES 2, 3 AND COMPARATIVE EXAMPLES 1, 2

Crystalline compositions of 2-hydroxynaphthalene-3-carboxylic acid were prepared according to the procedure of EXAMPLE 1 except that the temperature at the acid precipitating steps varied from 100° C. to 140° C.

EXAMPLE 4

To a 1 L autoclave, 105.6 g of 2-hydroxynaphthalene-3-carboxylic acid synthesized by the Kolbe-Schmitt method and isolated by acid precipitation at 100° C., 100 g of sodium sulfate and 794.4 g of water were fed and heated to 165° C. to give aqueous solution of 2-hydroxynaphthalene-3-carboxylic acid. This solution was cooled to 80° C. at the rate of 0.4° C./min. At the same temperature, the mixture was filtered to give 103.8 g of crystalline 2-hydroxynaphthalene-3-carboxylic acid.

EXAMPLE 5

To a 1 L autoclave, 21.1 g of 2-hydroxy naphthalene-3-carboxylic acid synthesized by the Kolbe-Schmitt method and isolated by acid precipitation at 100° C., 19.9 g of sodium sulfate and 959.0 g of water were fed and heated to 140° C. to give aqueous solution of 2-hydroxynaphthalene-3-carboxylic acid. This solution was cooled to 80° C. at the rate of 0.4° C./min. At the same temperature, the mixture was filtered to give 18.4 g of crystalline 2-hydroxynaphthalene-3-carboxylic acid.

EXAMPLE 6

To a 1 L autoclave, 878.8 g of aqueous solution containing 103.6 g of sodium 2-hydroxynaphthalene-3-carboxylate prepared by the Kolbe-Schmitt method was fed and heated to 100° C. An aqueous sulfuric acid solution (72%) was added dropwise to the solution over 50 minutes to adjust the pH to 3.5 and then, 111.6 g of methanol was added thereto. The mixture was heated to 140° C. to dissolve the 2-hydroxynaphthalene-3-carboxylic acid and then cooled to 80° C. at the rate of 0.4° C./min. The mixture was filtered at the same temperature to give 88.3 g of crystalline 2-hydroxynaphthalene-3-carboxylic acid.

EXAMPLE 7

To a 1 L autoclave, 878.8 g of aqueous solution containing 103.6 g of sodium 2-hydroxynaphthalene-3-carboxylate prepared by the Kolbe-Schmitt method was fed and heated to 100° C. An aqueous sulfuric acid (72%) was added dropwise to the solution over 50 minutes to adjust the pH to 3.5, then 71.5 g of acetophenone was added. The mixture was heated to 140° C. to dissolve the 2-hydroxynaphthalene-3-carboxylic acid, then was cooled to 80° C. at the rate of 0.4° C./min. The mixture was filtered at the same temperature to give 87.2 g of crystalline 2-hydroxynaphthalene-3-carboxylic acid.

EXAMPLE 8

To a 1 L kolben, 125 g of 2-hydroxynaphthalene-3-carboxylic acid synthesized by the Kolbe-Schmitt method and isolated by acid precipitation at 100° C., 175 g of water and 700 g of methanol were fed and heated to 70° C. to give a solution of 2-hydroxynaphthalene-3-carboxylic acid. The aqueous solution was cooled to 20° C. at the rate of 0.4° C./min.and filtered at the same temperature to give 108.1 g of crystalline 2-hydroxynaphthalene-3-carboxylic acid.

EXAMPLE 9

To a 1 L autoclave, 125 of 2-hydroxynaphthalene-3-carboxylic acid synthesized by the Kolbe-Schmitt method and isolated by acid precipitation at 100° C., 75 g of water and 300 g of methanol were fed and heated to 110° C. to give a solution of 2-hydroxynaphthalene-3-carboxylic acid. The aqueous solution was cooled to 20° C. at the rate of 0.4° C./min.and filtered at the same temperature to give 113.8 g of crystalline 2-hydroxynaphthalene-3-carboxylic acid.

Evaluation

Crystalline compositions of 2-hydroxynaphthalene-3-carboxylic acid obtained in the respective examples and comparative examples were examined. Their particle size, ML value, chromaticity properties including lightness and whiteness, particle characteristics and dusting tendency were determined/evaluated according to the following method:

Particle Size

Particle size was determined with sieves of 20 Mon (710 μm aperture), 48 Mon (297 μm aperture), 83 Mon (170 μm aperture), 140 Mon (106 μm aperture), 200 Mon (74 μm aperture) and 330 Mon (45 μm aperture), and a shaker (MEIDENSHA Type E4-SNR), by measuring the ratios of the residues on the respective sieves. In detail, firstly, the whole crystalline composition was screened with 710 μm sieve for 10 minutes at 230 rpm by means of the shaker and weight % of the residue on the sieve against the starting weight of the composition was determined. Then, the whole composition passed through the sieve was then screened with 297 μm sieve in the same manner. The composition was screened successively by the sieves listed above and lastly, was screened with 45 μm sieve and the amount of the composition passed the sieve was also determined.

Average particle sizes, proportion of the particles higher than 297 μm and those less than 74 μm are shown in table 1; particle size distribution is shown in table 2; ML value and chromaticity are shown in table 3 and the particle characteristics are shown in table 4. The average particle size means the value determined by the following formula:

average particle size (μm)=(710×residue on the 710 μm sieve (wt %)/100)+(297×residue on the 297 μm sieve (wt %)/100)+(170×residue on the 170 μm sieve (wt %)/100)+(106 μm×residue on the 106 μm sieve (wt %)/100)+

(74×residue on the 74 μm sieve (wt %)/100)+(45×residue on the 45 μm sieve (wt %)/100)+(25×passed 45 μm sieve (wt %)/100).

ML Value

ML value is obtained by multiplying the absorbance at 530 nm per 1 g of the compound by 200. In detail, 6 g of the sample was weighted and dissolved into methyl alcohol to give the total volume of 200 ml, filtered with No.5A filter paper (12.5 cm) and then, the absorbance of the solution was measured using methyl alcohol as a control. The ML value was determined according to the following formula:

ML value=absorbance/amount of the sample (g)×200

Results are shown in Table 3.

Chromaticity

Chromaticity characteristics, that is L, a, and b values and whiteness were determined by measuring the tristimulus values with color meter ZE2000 (NIHON DENSHOKU KOGYO KABUSHIKI KAISHA) and calculating according to the above definitions. Results are shown in table 3.

Particle Characteristics

Powdertester (Type PT-N, HOSOKAWA MICRON CO., Ltd) was used. The following values were determined according to the instruction attached to the device.

Aerated Bulk Density

The sample on the sieve was shaken to allow falling into a standard container through the shout, then the standard container was weighted to determine the aerated bulk density.

Packed Bulk Density

The sample was filled into a standard container, the container was tapped from the given height for the given times and then, the bulk density of the sample packed by tapping was determined.

Compression Rate

The compression rate is the value obtained according to the following formula:

(packed bulk density−aerated bulk density)/packed bulk density×100

Spatula Angle

The angle of the powder composition deposited on the spatula was measured. Results are summarized in Table 4.

Dissolution Time

Each of the 2-hydroxynaphthalene-3-carboxylic acid samples were weighed 10 g and added to 104 g of 5% aqueous sodium hydroxide and stirred. The time required to completely dissolve the each of the samples was visually determined. The results are shown in Table 4.

Evaluation of Dust Dispersion 50 g of each crystalline compositions was slid down along a slope of 60° for a distance of 50 cm. When the composition reached to the bottom, the height and distance to which the dust flew were measured. The results are shown in Table 5.

TABLE 1

|  | acid precipitation temp. (° C.) | average particle size (μm) | ≧297 μm (%) | ≦74 μm (%) |
| --- | --- | --- | --- | --- |
| Ex. 1 | 160 | 367.4 | 88.16 | 0.69 |
| Ex. 2 | 140 | 263.5 | 75.59 | 0.79 |
| Ex. 3 | 120 | 156.7 | 14.09 | 2.52 |
| Comp. Ex. 1 | 110 | 92.7 | 1.07 | 17.18 |
| Comp. Ex. 2 | 100 | 71.5 | 1.39 | 45.78 |
| Ex. 4 |  | 214.6 | 50.74 | 3.77 |
| Ex. 5 |  | 265.5 | 75.07 | 0.45 |
| Ex. 6 |  | 195.5 | 33.80 | 5.50 |
| Ex. 7 |  | 172.1 | 28.88 | 6.83 |
| Ex. 8 |  | 212.4 | 48.94 | 10.04 |
| Ex. 9 |  | 236.0 | 56.09 | 5.44 |

TABLE 2

|  | particle distribution (%) | | | | | | |
| --- | --- | --- | --- | --- | --- | --- | --- |
|  | 20 Mon (710μ) | 48 Mon (297μ) | 83 Mon (170μ) | 140 Mon (106μ) | 200 Mon (74μ) | 330 Mon (45μ) | passed 330 Mon |
| Ex. 1 | 21.43 | 66.73 | 8.12 | 2.15 | 0.88 | 0.59 | 0.10 |
| Ex. 2 | 0.20 | 75.39 | 20.31 | 2.83 | 0.49 | 0.59 | 0.20 |
| Ex. 3 | 0.00 | 14.09 | 43.35 | 32.85 | 7.19 | 1.94 | 0.58 |
| Comp. Ex. 1 | 0.10 | 0.97 | 7.38 | 44.95 | 29.42 | 14.27 | 2.91 |
| Comp. Ex. 2 | 0.30 | 1.09 | 3.47 | 17.74 | 31.62 | 33.39 | 12.39 |
| Ex. 4 | 0.74 | 50.00 | 21.91 | 14.71 | 8.87 | 2.71 | 1.0 |
| Ex. 5 | 0.51 | 74.56 | 22.47 | 1.58 | 0.43 | 0.43 | 0.2 |
| Ex. 6 | 0.20 | 33.60 | 45.00 | 13.20 | 2.50 | 3.10 | 2.4 |
| Ex. 7 | 0.20 | 28.68 | 26.71 | 30.17 | 7.41 | 4.45 | 2.38 |
| Ex. 8 | 0.72 | 48.22 | 28.44 | 8.82 | 3.76 | 5.50 | 4.54 |
| Ex. 9 | 2.90 | 53.19 | 24.89 | 9.01 | 4.57 | 3.96 | 1.48 |

TABLE 3

|  | ML value | L lightness | a redness | b yellowness | HW whiteness |
| --- | --- | --- | --- | --- | --- |
| Ex. 1 | — | 40.41 | 4.12 | 16.32 | 6.91 |
| Ex. 2 | 1.33 | 56.23 | 0.21 | 26.79 | 10.09 |
| Ex. 3 | 1.23 | 66.14 | 3.87 | 31.66 | 13.83 |
| Comp. Ex. 1 | 1.17 | 76.13 | 0.43 | 34.21 | 20.75 |
| Comp. Ex. 2 | 1.03 | 80.82 | −0.51 | 36.68 | 22.97 |
| Ex. 4 | 1.80 | 38.15 | 6.61 | 18.26 | 4.61 |
| Ex. 5 | 1.17 | 56.45 | 3.77 | 25.51 | 11.29 |
| Ex. 6 | 1.37 | 54.49 | 7.38 | 28.25 | 7.70 |

TABLE 3-continued

|  | | chromaticity | | | |
| --- | --- | --- | --- | --- | --- |
|  | ML value | L lightness | a redness | b yellowness | HW whiteness |
| Ex. 7 | 1.40 | 62.84 | 5.43 | 28.81 | 13.62 |
| Ex. 8 | 0.23 | 84.42 | −4.70 | 36.21 | 27.59 |
| Ex. 9 | 0.40 | 76.85 | −2.71 | 30.43 | 25.65 |

TABLE 4

|  | bulk density (g/cc) | | aerated/ packed | compression rate | spatula angle | dissolution time |
| --- | --- | --- | --- | --- | --- | --- |
|  | aerated | packed | (%) | (%) | (deg) |  |
| Ex. 1 | 0.547 | 0.601 | 91.01 | 9.0 | 50.4 | 17'35" |
| Ex. 2 | 0.514 | 0.578 | 88.93 | 11.1 | 48.4 | 8'55" |
| Ex. 3 | 0.341 | 0.474 | 71.94 | 28.1 | 61.6 | 12'11" |
| Comp. Ex. 1 | 0.312 | 0.422 | 73.93 | 26.1 | 63.3 | 25' |
| Comp. Ex. 2 | 0.262 | 0.429 | 61.07 | 38.9 | 74.2 | 29' |
| Ex. 4 | — | — | — | — | — | 15'39" |
| Ex. 5 | 0.355 | 0.459 | 77.34 | 22.7 | 66.5 | 9'44" |
| Ex. 6 | 0.493 | 0.554 | 88.99 | 11.0 | 47.4 | 16'9" |
| Ex. 7 | 0.622 | 0.687 | 90.54 | 9.5 | 47.1 | 7'28" |
| Ex. 8 | 0.591 | 0.699 | 54.55 | 15.4 | 62.3 | 15'39" |
| Ex. 9 | 0.478 | 0.618 | 77.35 | 22.6 | 50.0 | 7'49" |

TABLE 5

|  | distance (cm) | height (cm) |
| --- | --- | --- |
| Ex. 1 | 5 | 10 |
| Ex. 2 | 10 | 7 |
| Ex. 3 | 30 | 15 |
| Comp. Ex. 1 | 50 | 30 |
| Comp. Ex. 2 | >100 | 25 |
| Ex. 4 | 20 | 13 |
| Ex. 5 | 15 | 10 |
| Ex. 6 | 30 | 15 |
| Ex. 7 | 35 | 15 |
| Ex. 8 | 20 | 17 |
| Ex. 9 | 15 | 12 |

Dust of the respective crystalline 2-hydroxynaphthalene-3-carboxylic acid of the examples dispersed 5–35 cm in distance and 7–17 cm in height. It is revealed that the dusting tendency of the crystalline composition was significantly suppressed. On the other hand, dust of the crystalline 2-hydrpxynaphthalene-3-carboxylic acid of the comparative examples flew widely to more than 50 cm in distance and more than 25 cm in height.

INDUSTRIAL APPLICABILITY

The compound of the present invention, 2-hydroxynaphthalene-3-carboxylic acid, is industrially useful as an intermediate for pigments or dyes. Since the crystalline 2-hydroxynaphthalene-3-carboxylic acid of the present invention shows significantly suppressed dusting tendency, the crystalline compound is easy to handle and affect significantly reduced influence to environment and human beings.

What is claimed is:

1. Crystalline 2-hydroxynaphthalene-3-carboxylic acid, characterized in that the average particle size is equal to or more than 157 μm and that the proportion of the particles of which particle size are equal to or less than 74 μm is equal to or less than 14%.

2. The crystalline 2-hydroxynaphthalene-3-carboxylic acid of claim 1, characterized in that the lightness is 38–69 and whiteness is 4.6–18.0.

3. The crystalline 2-hydroxynaphthalene-3-carboxylic acid of claim 1, characterized in that the dissolution time determined by dissolving 10 g of the 2-hydroxynaphthalene-3-carboxylic acid in 104 g of 5% aqueous sodium hydroxide at an ambient temperature is less than 20 minutes.

4. A method for preparing the crystalline 2-hydroxynaphthalene-3-carboxylic acid of claim 1, which comprises the step of recrystallizing 2-hydroxynaphthalene-3-carboxylic acid at a high temperature.

5. A method for preparing the crystalline 2-hydroxynaphthalene-3-carboxylic acid of claim 1 comprising the step of acid precipitating an alkaline metal salt of 2-hydroxynaphthalene-3-carboxylic acid, characterized in that further comprising the step of recrystallizing 2-hydroxynaphthalene-3-carboxylic acid at a high temperature immediately after the acid precipitating step.

6. A method for preparing the crystalline 2-hydroxynaphthalene-3-carboxylic acid of claim 1 comprising the step of acid precipitating an alkaline metal salt of 2-hydroxynaphthalene-3-carboxylic acid, characterized in that the acid precipitation step is carried out at the temperature of higher than 120° C.

7. A method for preparing the crystalline 2-hydroxynaphthalene-3-carboxylic acid of claim 1 comprising the step of acid precipitating an alkaline metal salt of 2-hydroxynaphthalene-3-carboxylic acid, characterized in that further comprising the step of recrystallizing the crystal obtained in the acid precipitation step.

* * * * *

UNITED STATES PATENT AND TRADEMARK OFFICE
CERTIFICATE OF CORRECTION

PATENT NO. : 6,403,827 B1  
DATED : June 11, 2002  
INVENTOR(S) : Ryuzo Ueno et al.

It is certified that error appears in the above-identified patent and that said Letters Patent is hereby corrected as shown below:

<u>Title page,</u>  
Item [73], Assignee, please change "Kabushiki Kaisha Ueno Seiyaku Oyo K." to -- Kabushiki Kaisha Ueno Seiyaku Kenkyujo --

Signed and Sealed this

Nineteenth Day of August, 2003

JAMES E. ROGAN  
*Director of the United States Patent and Trademark Office*

UNITED STATES PATENT AND TRADEMARK OFFICE
CERTIFICATE OF CORRECTION

PATENT NO. : 6,403,827 B1
DATED : June 11, 2002
INVENTOR(S) : Ryuzo Ueno et al.

It is certified that error appears in the above-identified patent and that said Letters Patent is hereby corrected as shown below:

<u>Title page,</u>
Item [73], Assignee, delete "Kabushiki Kaisha Ueno Seiyaku Kenkyujo" and insert
-- Kabushiki Kaisha Ueno Seiyaku Oyo Kenkyujo --

Signed and Sealed this

Eighth Day of June, 2004

JON W. DUDAS
*Acting Director of the United States Patent and Trademark Office*